United States Patent
Zoran et al.

(10) Patent No.: US 9,770,285 B2
(45) Date of Patent: Sep. 26, 2017

(54) SYSTEM AND METHOD FOR IDENTIFYING AND CONTROLLING AN ELECTROSURGICAL APPARATUS

(71) Applicant: Bovie Medical Corporation, Clearwater, FL (US)

(72) Inventors: Arik Zoran, Clearwater, FL (US); Gregory A. Konesky, Hampton Bays, NY (US)

(73) Assignee: Bovie Medical Corporation, Clearwater, FL (US)

( * ) Notice: Subject to any disclaimer, the term of this patent is extended or adjusted under 35 U.S.C. 154(b) by 0 days.

(21) Appl. No.: 14/715,847

(22) Filed: May 19, 2015

(65) Prior Publication Data

US 2015/0257817 A1 Sep. 17, 2015

Related U.S. Application Data

(63) Continuation-in-part of application No. 13/802,572, filed on Mar. 13, 2013, now Pat. No. 9,144,453, (Continued)

(51) Int. Cl.
*A61B 18/14* (2006.01)
*A61B 18/04* (2006.01)
(Continued)

(52) U.S. Cl.
CPC ........ *A61B 18/1402* (2013.01); *A61B 18/042* (2013.01); *A61B 17/3209* (2013.01);
(Continued)

(58) Field of Classification Search
CPC ... A61B 18/1402; A61B 18/042; A61B 18/14; A61B 18/12; A61B 18/04;
(Continued)

(56) References Cited

U.S. PATENT DOCUMENTS

| | | | |
|---|---|---|---|
| 1,813,902 A | 7/1931 | Bovie | |
| 2,435,442 A | 2/1948 | Gurewitsch | |

(Continued)

FOREIGN PATENT DOCUMENTS

| | | |
|---|---|---|
| EP | 0878263 | 11/1998 |
| EP | 1764057 | 3/2007 |

(Continued)

OTHER PUBLICATIONS

Kirschner, Jared; Surface Acoustic Wave Sensors (SAWS): Design for Application, Microelectromechanical Systems, Dec. 6, 2010; pp. 1-11.

*Primary Examiner* — Scott Getzow
(74) *Attorney, Agent, or Firm* — Gerald E. Hespos; Michael J. Porco; Matthew T. Hespos

(57) ABSTRACT

An electrosurgical apparatus including an automatic applicator identifier used to communicate between an applicator and a generator unit, automatically presetting various values, is provided. These values may be stored in a one-wire serial memory storage device located in the applicator or connector coupled to the applicator. Communication from the applicator to the generator unit of these values is affected by a one-wire serial communication protocol. This information can be transferred over a direct electrical path through the connector that attaches that applicator to the generator unit, or instead by a wireless link.

29 Claims, 10 Drawing Sheets

Related U.S. Application Data which is a continuation-in-part of application No. 13/289,060, filed on Nov. 4, 2011, now Pat. No. 9,060,765, application No. 14/715,847, which is a continuation-in-part of application No. 13/802,227, filed on Mar. 13, 2013, now Pat. No. 9,095,333.

(60) Provisional application No. 61/411,174, filed on Nov. 8, 2010, provisional application No. 61/667,213, filed on Jul. 2, 2012, provisional application No. 61/716,688, filed on Oct. 22, 2012.

(51) Int. Cl.
| | |
|---|---|
| A61B 18/00 | (2006.01) |
| A61B 18/12 | (2006.01) |
| A61B 17/3209 | (2006.01) |
| A61B 17/00 | (2006.01) |
| A61B 90/00 | (2016.01) |

(52) U.S. Cl.
CPC ........... A61B 2017/00221 (2013.01); A61B 2018/00178 (2013.01); A61B 2018/00589 (2013.01); A61B 2018/00607 (2013.01); A61B 2018/00946 (2013.01); A61B 2018/00988 (2013.01); A61B 2018/1286 (2013.01); A61B 2018/1475 (2013.01); A61B 2090/0811 (2016.02)

(58) Field of Classification Search
CPC ............ A61B 18/1233; A61B 17/3209; A61B 2017/00221; A61B 2018/00178; A61B 2018/00589; A61B 2018/00607; A61B 2018/00946; A61B 2018/00988; A61B 2018/1286; A61B 2018/1475
See application file for complete search history.

(56) References Cited

U.S. PATENT DOCUMENTS

| | | | |
|---|---|---|---|
| 3,239,730 A | 3/1966 | Farago | |
| 3,801,766 A | 4/1974 | Morrison, Jr. | |
| 4,127,110 A | 11/1978 | Bullara | |
| 4,545,375 A | 10/1985 | Cline | |
| 4,580,562 A | 4/1986 | Goof et al. | |
| 4,619,258 A | 10/1986 | Pool | |
| 4,625,723 A | 12/1986 | Altnether et al. | |
| 4,632,109 A | 12/1986 | Paterson | |
| 4,708,137 A | 11/1987 | Tsukagoshi | |
| 4,827,927 A | 5/1989 | Newton | |
| 5,088,997 A | 2/1992 | Delahuerga et al. | |
| 5,098,430 A | 3/1992 | Fleenor | |
| 5,207,675 A | 5/1993 | Canady | |
| 5,256,138 A | 10/1993 | Burek et al. | |
| 5,269,780 A | 12/1993 | Roos | |
| 5,306,238 A | 4/1994 | Fleenor | |
| 5,400,267 A | 3/1995 | Denen et al. | |
| 5,425,375 A | 6/1995 | Chin et al. | |
| 5,449,356 A | 9/1995 | Walbrink et al. | |
| 5,626,575 A | 5/1997 | Crenner | |
| 5,647,869 A | 7/1997 | Goble et al. | |
| 5,651,780 A | 7/1997 | Jackson et al. | |
| 5,660,657 A | 8/1997 | Rajala et al. | |
| 5,693,042 A | 12/1997 | Boiarski et al. | |
| 5,693,044 A | 12/1997 | Cosmescu | |
| 5,776,092 A | 7/1998 | Farin et al. | |
| 5,800,427 A | 9/1998 | Zamba | |
| 6,193,715 B1 | 2/2001 | Wrublewski et al. | |
| 6,225,593 B1 | 5/2001 | Howieson et al. | |
| 6,293,945 B1 | 9/2001 | Parins et al. | |
| 6,325,799 B1 | 12/2001 | Goble | |
| 6,391,027 B1 | 5/2002 | Farin et al. | |
| 6,409,724 B1 | 6/2002 | Penny et al. | |
| 6,458,125 B1 | 10/2002 | Cosmescu | |
| 6,475,215 B1 | 11/2002 | Tanrisever | |
| 6,558,383 B2 | 5/2003 | Cunningham et al. | |
| 6,578,579 B2 | 6/2003 | Burnside et al. | |
| 6,652,514 B2 | 11/2003 | Ellman et al. | |
| 6,740,079 B1 | 5/2004 | Eggers | |
| 6,770,071 B2 | 8/2004 | Woloszko et al. | |
| 6,899,538 B2 | 5/2005 | Matoba | |
| 6,958,063 B1 | 10/2005 | Soll et al. | |
| 6,994,707 B2 | 2/2006 | Ellman et al. | |
| 7,033,353 B2 | 4/2006 | Stoddard et al. | |
| 7,115,121 B2 | 10/2006 | Novak | |
| 7,156,842 B2 | 1/2007 | Sartor et al. | |
| 7,156,844 B2 | 1/2007 | Reschke et al. | |
| 7,169,144 B2* | 1/2007 | Hoey ................ A61B 18/1206 606/34 |
| 7,244,257 B2 | 7/2007 | Podhajsky et al. | |
| 7,316,682 B2 | 1/2008 | Konesky | |
| 7,335,199 B2 | 2/2008 | Goble et al. | |
| 7,443,296 B2 | 10/2008 | Mezhinsky et al. | |
| 7,479,140 B2 | 1/2009 | Ellman et al. | |
| 7,481,809 B2 | 1/2009 | Stern et al. | |
| 7,503,917 B2 | 3/2009 | Sartor et al. | |
| 7,568,619 B2 | 8/2009 | Todd et al. | |
| 7,578,817 B2 | 8/2009 | Canady | |
| 7,654,975 B2* | 2/2010 | Mantell ............... A61M 13/003 604/26 |
| 7,749,221 B2 | 7/2010 | Rontal | |
| 7,815,638 B2 | 10/2010 | Farin et al. | |
| 8,016,824 B2 | 9/2011 | Buchman, II et al. | |
| 8,022,327 B2 | 9/2011 | Blomeyer | |
| 8,177,782 B2 | 5/2012 | Beller et al. | |
| 8,216,220 B2 | 7/2012 | Jensen et al. | |
| 8,319,134 B2 | 11/2012 | Blomeyer | |
| 8,353,905 B2 | 1/2013 | Jensen et al. | |
| 8,562,598 B2 | 10/2013 | Falkenstein et al. | |
| 8,568,400 B2* | 10/2013 | Gilbert ................. A61B 18/12 606/34 |
| 8,689,606 B2 | 4/2014 | Schellekens et al. | |
| 2002/0013582 A1 | 1/2002 | Mulier et al. | |
| 2003/0050633 A1 | 3/2003 | Ellman et al. | |
| 2003/0130655 A1 | 7/2003 | Woloszko et al. | |
| 2004/0148903 A1 | 8/2004 | Cash | |
| 2004/0243120 A1 | 12/2004 | Orszulak et al. | |
| 2005/0075630 A1 | 4/2005 | Truckai et al. | |
| 2005/0148903 A1 | 7/2005 | Diamantopoulos | |
| 2006/0122595 A1* | 6/2006 | Farin ................... A61B 18/042 606/45 |
| 2007/0028669 A1 | 2/2007 | Brewster | |
| 2007/0049926 A1 | 3/2007 | Sartor | |
| 2007/0083247 A1 | 4/2007 | Wyeth et al. | |
| 2007/0093810 A1 | 4/2007 | Sartor et al. | |
| 2007/0135812 A1 | 6/2007 | Sartor | |
| 2007/0158209 A1 | 7/2007 | Kang et al. | |
| 2007/0260239 A1 | 11/2007 | Podhajsky et al. | |
| 2008/0071261 A1 | 3/2008 | Orszulak | |
| 2008/0108985 A1 | 5/2008 | Konesky | |
| 2008/0140066 A1 | 6/2008 | Davison et al. | |
| 2009/0005772 A1 | 1/2009 | Penny | |
| 2009/0125023 A1 | 5/2009 | Stephen et al. | |
| 2009/0143778 A1 | 6/2009 | Sartor et al. | |
| 2009/0149851 A1 | 6/2009 | Craig | |
| 2009/0248022 A1* | 10/2009 | Falkenstein ........ A61B 18/1445 606/51 |
| 2010/0094288 A1 | 4/2010 | Kerr | |
| 2010/0262139 A1 | 10/2010 | Beller et al. | |
| 2011/0238053 A1 | 9/2011 | Brannan et al. | |
| 2011/0276113 A1 | 11/2011 | Cybulski | |
| 2012/0116397 A1 | 5/2012 | Rencher et al. | |
| 2012/0123405 A1 | 5/2012 | Moua et al. | |
| 2012/0232540 A1 | 9/2012 | Baur et al. | |
| 2012/0330305 A1 | 12/2012 | Zoran et al. | |
| 2012/0330307 A1 | 12/2012 | Ladtkow et al. | |
| 2013/0046290 A1 | 2/2013 | Palmer et al. | |
| 2013/0237982 A1 | 9/2013 | Rencher et al. | |
| 2013/0296846 A1 | 11/2013 | Canady et al. | |

(56) References Cited

U.S. PATENT DOCUMENTS

2014/0005665 A1    1/2014    Konesky et al.
2014/0018795 A1    1/2014    Shilev et al.

FOREIGN PATENT DOCUMENTS

| EP | 2263728 | 12/2010 |
| EP | 2449992 | 5/2012 |
| WO | 2004096315 | 11/2004 |

\* cited by examiner

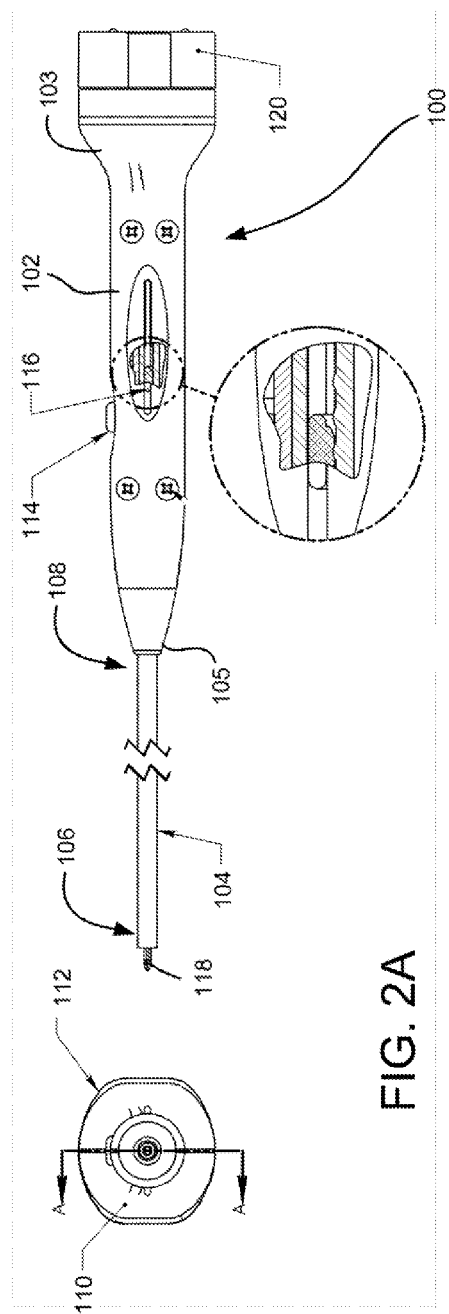
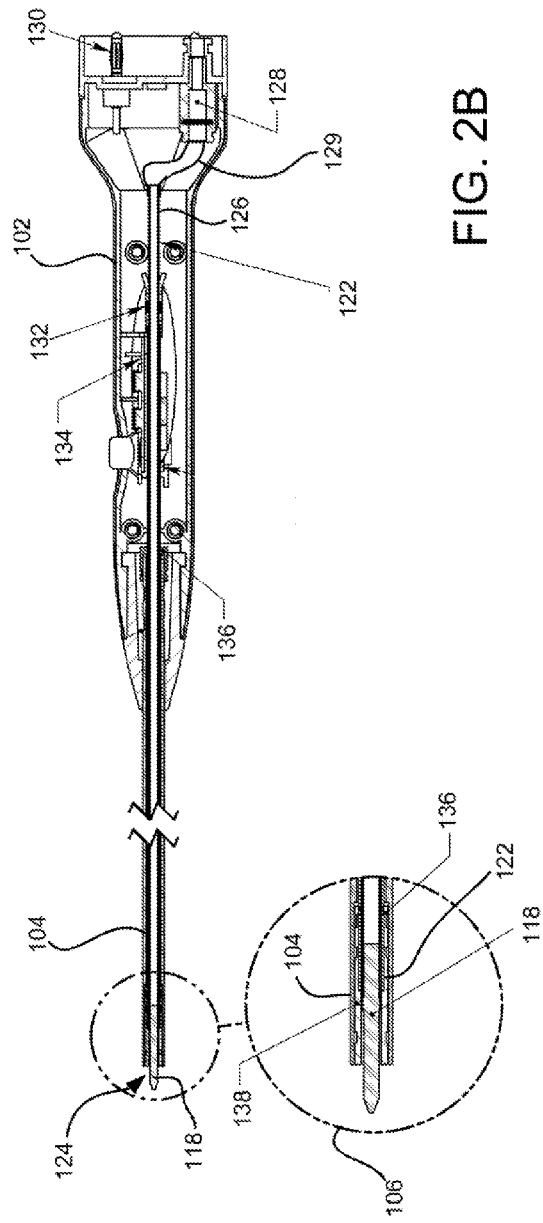
FIG. 2A
FIG. 2B

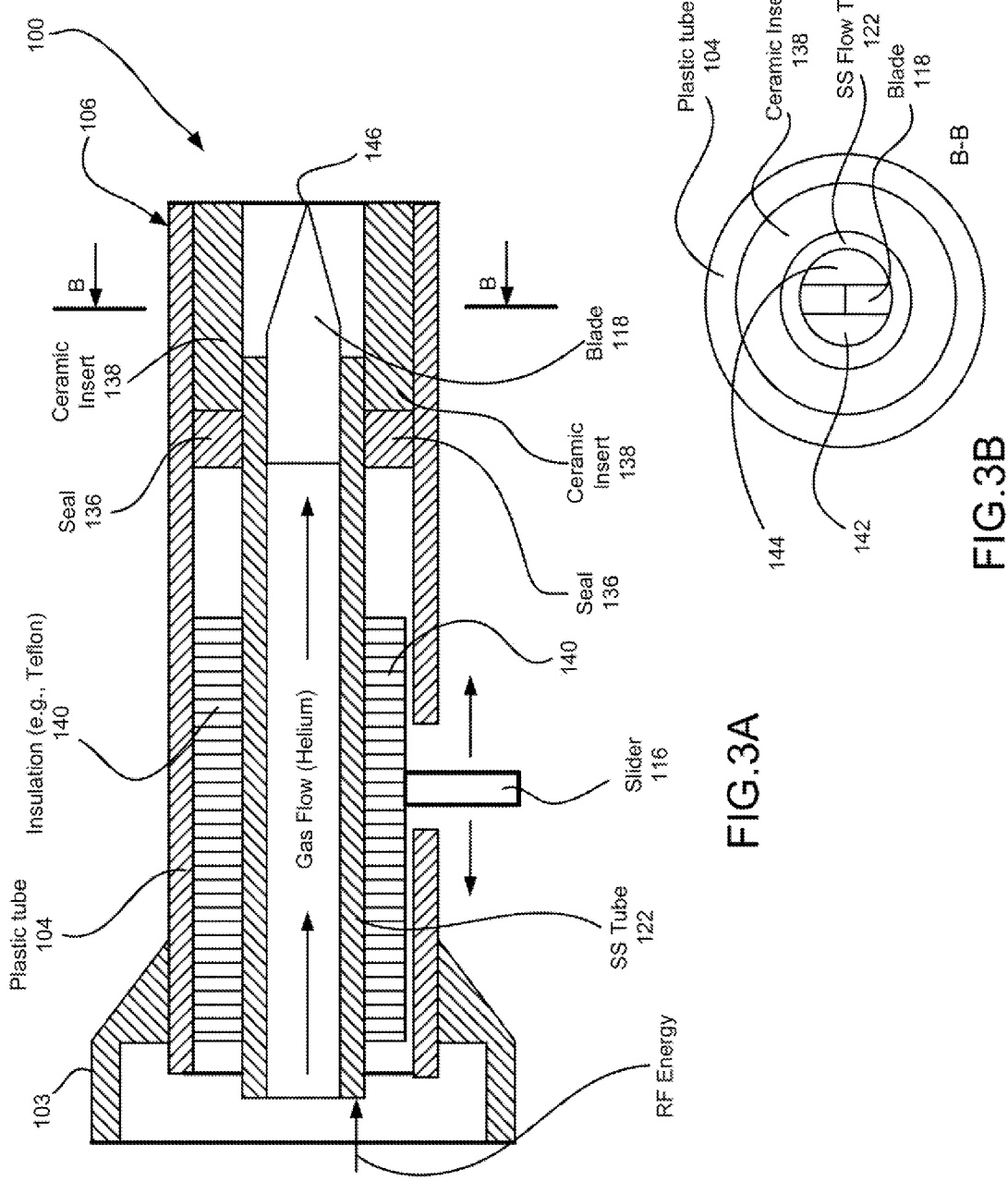

SYSTEM AND METHOD FOR IDENTIFYING AND CONTROLLING AN ELECTROSURGICAL APPARATUS

PRIORITY

This application is a continuation-in-part application of U.S. application Ser. No. 13/802,572 filed Mar. 13, 2013, which is a continuation-in-part application of U.S. application Ser. No. 13/289,060 filed Nov. 4, 2011, which claims priority on U.S. Provisional Patent Appl. No. 61/411,174, filed Nov. 8, 2010, the content of all of which are hereby incorporated by reference in their entireties.

This application is also a continuation-in-part application of U.S. application Ser. No. 13/802,227 filed Mar. 13, 2013, which claims priority on U.S. Provisional Patent Appl. No. 61/667,213, filed Jul. 2, 2012 and U.S. Provisional Patent Appl. No. 61/716,688, filed Oct. 22, 2012, the content of all of which are hereby incorporated by reference in their entireties.

BACKGROUND

Field

The present disclosure relates generally to electrosurgery and electrosurgical systems and apparatuses, and more particularly, to an electrosurgical apparatus including an automatic applicator identifier used to communicate between the applicator and a generator unit, automatically presetting various values.

Description of the Related Art

High frequency electrical energy has been widely used in surgery. Tissue is cut and bodily fluids are coagulated using electrosurgical energy.

Electrosurgical instruments generally comprise "monopolar" devices or "bipolar" devices. Monopolar devices comprise an active electrode on the electrosurgical instrument with a return electrode attached to the patient. In monopolar electrosurgery, the electrosurgical energy flows through the active electrode on the instrument through the patient's body to the return electrode. Such monopolar devices are effective in surgical procedures where cutting and coagulation of tissue are required and where stray electrical currents do not pose a substantial risk to the patient.

Bipolar devices comprise an active electrode and a return electrode on the surgical instrument. In a bipolar electrosurgical device, electrosurgical energy flows through the active electrode to the tissue of a patient through a short distance through the tissue to the return electrode. The electrosurgical effects are substantially localized to a small area of tissue that is disposed between the two electrodes on the surgical instrument. Bipolar electrosurgical devices have been found to be useful with surgical procedures where stray electrical currents may pose a hazard to the patient or where other procedural concerns require close proximity of the active and return electrodes. Surgical operations involving bipolar electrosurgery often require methods and procedures that differ substantially from the methods and procedures involving monopolar electrosurgery.

Gas plasma is an ionized gas capable of conducting electrical energy. Plasmas are used in surgical devices to conduct electrosurgical energy to a patient. The plasma conducts the energy by providing a pathway of relatively low electrical resistance. The electrosurgical energy will follow through the plasma to cut, coagulate, desiccate, or fulgurate blood or tissue of the patient. There is no physical contact required between an electrode and the tissue treated.

Electrosurgical systems that do not incorporate a source of regulated gas can ionize the ambient air between the active electrode and the patient. The plasma that is thereby created will conduct the electrosurgical energy to the patient, although the plasma arc will typically appear more spatially dispersed compared with systems that have a regulated flow of ionizable gas.

Atmospheric pressure discharge cold plasma applicators have found use in a variety of applications including surface sterilization, hemostasis, and ablation of tumors. In the latter example, the process can be relatively slow, generate large volumes of noxious smoke with vaporized and charred tissue, and may cause collateral damage to surrounding healthy tissue when high power electrosurgical energy is used. Precision accuracy can also be a problem, due to the width of the plasma beam. Often, a simple surgical knife is used to excise the tissue in question, followed by the use of a cold plasma applicator for cauterization, sterilization, and hemostasis.

Medical devices used in the afore-mentioned electrosurgery and plasma-beam surgery typically consist of a generator unit and an attached hand piece or applicator. A variety of different applicators may be available for a given generator unit, some of which are general purpose, and others designed for a specific task. Those designed for a specific task may have limitations with regard to maximum power and/or gas flow rate, as in the case of plasma-beam applicators. Also, there may be changes in the characteristics of the applicator with prolonged use, affecting its safety and effectiveness. Finally, some applicators that are disposable cannot be re-sterilized and its use must be limited to a single procedure.

Rather than rely on the operators' correct presetting of the generator unit for a specific applicator type, a need exists for an automatic applicator identifier to communicate between the applicator and the generator unit, automatically presetting various values.

SUMMARY

The present disclosure relates to an electrosurgical apparatus with a retractable blade for use in cold plasma applications, electrosurgical cutting, electrosurgical coagulation and mechanical cutting. When the blade is retracted within the electrosurgical apparatus, it is electrically energized while an inert gas flows over it, producing a cold plasma discharge. In the de-energized state, the blade is advanced and used as a traditional surgical blade making contact with tissue to achieve mechanical cutting. Additionally, the blade may be advanced and used while both electrically energized and with inert gas flow. In this mode, the apparatus may be employed for electrosurgical cutting or coagulation.

In one aspect of the present disclosure, an automatic applicator identifier is used to communicate between the apparatus or applicator and a generator unit, automatically presetting various values. These values may be stored in a one-wire serial memory storage device located in the applicator. Communication from the applicator to the generator unit of these values is affected by a one-wire serial communication protocol. It is to be appreciated that the serial communication protocol may be bidirectional, i.e., data may be read from the one-wire serial memory storage device and written to the one-wire serial memory storage device. This information can be transferred over a direct electrical path through the connector that attaches the applicator to the generator unit, or instead by a wireless link. Communication of these preset values is transferred from the applicator to the generator unit upon power-up initialization of the generator unit, whenever the generator unit is reset, or when requested by the generator unit. The communication link can be encrypted to prevent unauthorized modification of the preset values. The automatic applicator identifier can also provide unique device identification and traceability.

Examples of preset applicator-specific values include maximum and/or minimum power settings, maximum and/or minimum gas flow rates, maximum activation duration, maximum number of activations, maximum accumulated run time, maximum number of uses in different procedures, or the ability to be re-used in subsequent procedures after the generator unit is powered-down. Other examples include power curve definition for a given class of applicator, and fine-tuning characteristics unique to a given applicator to optimize its performance.

In another aspect of the present disclosure, the memory device may have read/write capabilities where the memory device can store, for example, how many times a handpiece or applicator has been used and provide that information to an electrosurgical generator. In certain embodiments, the electrosurgical generator may store or write the number of uses or a period of time of use of the applicator in the memory device of the applicator, which may be subsequently used by the electrosurgical generator to determine that the applicator may no longer be used based on a predetermined use or time limit.

The automatic applicator identifier permits a general purpose adaptable interface between the applicator and generator unit so that a single generator unit can be used with a wide variety of applicator types, yet maintain optimum performance, safety, and effectiveness.

BRIEF DESCRIPTION OF THE DRAWINGS

The above and other aspects, features, and advantages of the present disclosure will become more apparent in light of the following detailed description when taken in conjunction with the accompanying drawings in which:

FIG. 2A is a schematic diagram of an electrosurgical apparatus in accordance with an embodiment of the present disclosure;

FIG. 2B is a cross sectional view of the electrosurgical apparatus shown in FIG. 2A taken along line A-A;

FIG. 3A is an enlarged cross sectional view of the electrosurgical apparatus in accordance with an embodiment of the present disclosure;

FIG. 3B illustrates a front view of the electrosurgical apparatus shown in FIG. 3A taken along line B-B;

Figure 1:
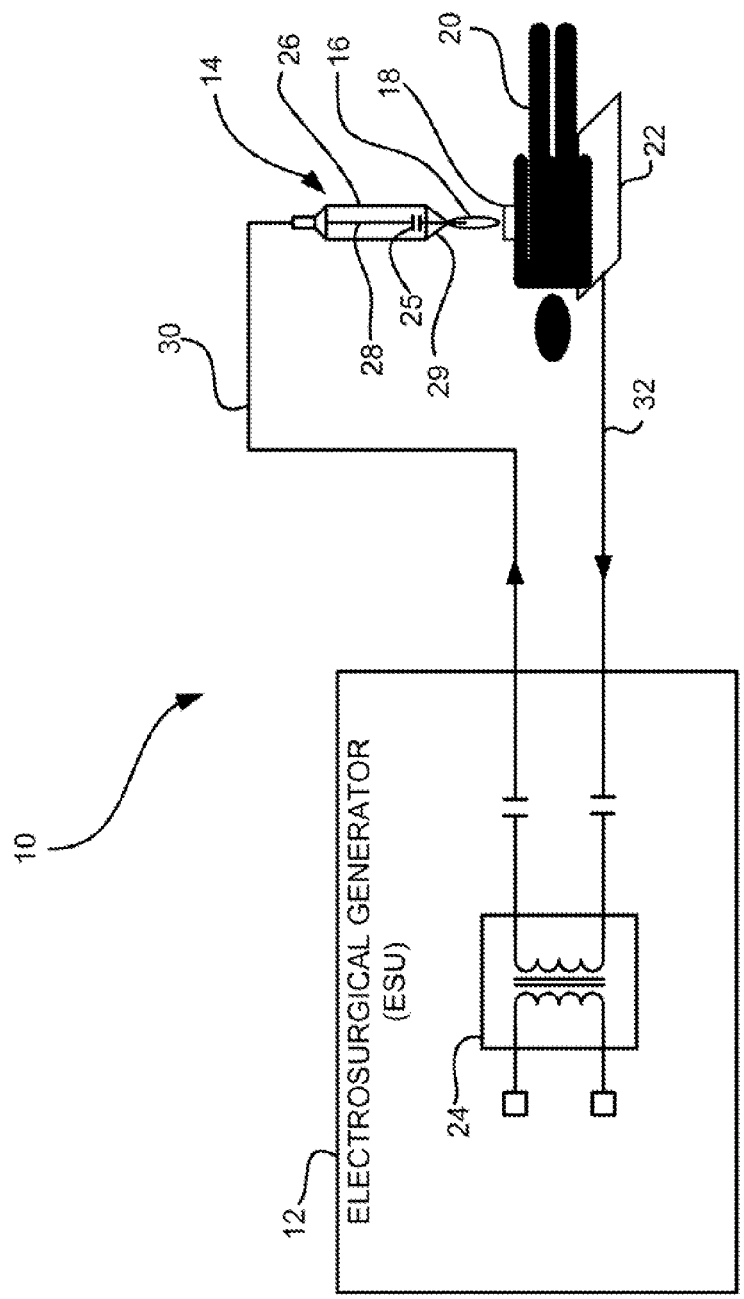
FIG. 1 is an illustration of an exemplary monopolar electrosurgical system in accordance with an embodiment of the present disclosure.

It should be understood that the drawing(s) is for purposes of illustrating the concepts of the disclosure and is not necessarily the only possible configuration for illustrating the disclosure.

DETAILED DESCRIPTION

Preferred embodiments of the present disclosure will be described hereinbelow with reference to the accompanying drawings. In the following description, well-known functions or constructions are not described in detail to avoid obscuring the present disclosure in unnecessary detail. In the drawings and in the description which follow, the term "proximal", as is traditional, will refer to the end of the device, e.g., instrument, apparatus, applicator, handpiece, forceps, etc., which is closer to the user, while the term "distal" will refer to the end which is further from the user. Herein, the phrase "coupled" is defined to mean directly connected to or indirectly connected with through one or more intermediate components. Such intermediate components may include both hardware and software based components.

FIG. 1 shows an exemplary monopolar electrosurgical system generally indicated as 10 comprising an electrosurgical generator (ESU) generally indicated as 12 to generate power for the electrosurgical apparatus 10 and a plasma generator generally indicated as 14 to generate and apply a plasma stream 16 to a surgical site or target area 18 on a patient 20 resting on a conductive plate or support surface 22. The electrosurgical generator 12 includes a transformer generally indicated as 24 including a primary and secondary coupled to an electrical source (not shown) to provide high frequency electrical energy to the plasma generator 14. Typically, the electrosurgical generator 12 comprises an isolated floating potential not referenced to any potential. Thus, current flows between the active and return electrodes. If the output is not isolated, but referenced to "earth", current can flow to areas with ground potential. If the contact surface of these areas and the patient is relatively small, an undesirable burning can occur.

The plasma generator 14 comprises a handpiece or holder 26 having an electrode 28 at least partially disposed within a fluid flow housing 29 and coupled to the transformer 24 to receive the high frequency electrical energy therefrom to at least partially ionize noble gas fed to the fluid flow housing 29 of the handpiece or holder 26 to generate or create the plasma stream 16. The high frequency electrical energy is fed from the secondary of the transformer 24 through an active conductor 30 to the electrode 28 (collectively active electrode) in the handpiece 26 to create the plasma stream 16 for application to the surgical site 18 on the patient 20. Furthermore, a current limiting capacitor 25 is provided in series with the electrode 28 to limit the amount of current being delivery to the patient 20.

The return path to the electrosurgical generator 12 is through the tissue and body fluid of the patient 20, the conductor plate or support member 22 and a return conductor 32 (collectively return electrode) to the secondary of the transformer 24 to complete the isolated, floating potential circuit.

In another embodiment, the electrosurgical generator 12 comprises an isolated non-floating potential not referenced to any potential. The plasma current flow back to the electrosurgical generator 12 is through the tissue and body fluid and the patient 20. From there, the return current circuit is completed through the combined external capacitance to the plasma generator handpiece 26, surgeon and through displacement current. The capacitance is determined, among other things, by the physical size of the patient 20. Such an electrosurgical apparatus and generator are described in commonly owned U.S. Pat. No. 7,316,682 to Konesky, the contents of which are hereby incorporated by reference.

It is to be appreciated that transformer 24 may be disposed in the plasma generator handpiece 26, as will be described in various embodiments below. In this configuration, other transformers may be provided in the generator 12 for providing a proper voltage and current to the transformer in the handpiece, e.g., a step-down transformer, a step-up transformer or any combination thereof.

Referring to FIG. 2A, an electrosurgical apparatus 100 in accordance with the present disclosure is illustrated. Generally, the apparatus 100 includes a housing 102 having a proximal end 103 and a distal end 105 and a tube 104 having an open distal end 106 and a proximal end 108 coupled to the distal end 105 of the housing 102. The housing 102 includes a right side housing 110 and left side housing 112, and further includes provisions for a button 114 and slider 116. Activation of the slider 116 will expose a blade 118 at the open distal end 106 of the tube 104. Activation of the button 114 will apply electrosurgical energy to the blade 118 and, in certain embodiments, enable gas flow through the flow tube 122, as will be described in detail below.

Additionally, a transformer 120 is provided on the proximal end 103 of the housing for coupling a source of radio frequency (RF) energy to the apparatus 100. By providing the transformer 120 in the apparatus 100 (as opposed to locating the transformer in the electrosurgical generator), power for the apparatus 100 develops from higher voltage and lower current than that required when the transformer is located remotely in the generator, which results in lower thermalization effects. In contrast, a transformer back in the generator produces applicator power at a lower voltage, higher current with greater thermalization effects. Therefore, by providing the transformer 120 in apparatus 100, collateral damage to tissue at the operative site is minimized.

A cross section view along line A-A of the apparatus 102 is shown in FIG. 2B. Disposed within the housing 102 and tube 104 is flow tube 122 which runs along the longitudinal axis of the apparatus 100. On a distal end 124 of the flow tube 122, the blade 118 is retained within the flow tube 122. A proximal end 126 of the flow tube 122 is coupled to a source of gas via a tube connector 128 and flexible tubing 129. The proximal end 126 of the flow tube 122 is also coupled to a source of RF energy via plug 130 which couples to transformer 120. The flow tube 122 is made of an electrically conducting material, preferably stainless steel, as to conduct the RF energy to the blade 118 when being employed for plasma applications or electrosurgical cutting as will be described below. The outer tube 104 is constructed from non-conductive material, e.g., Lestran. The slider 116 is coupled to the flow tube 122 via a retaining collar 132. A printed circuit board (PCB) 134 is disposed in the housing 102 and controls the application of the RF energy from the transformer 120 via the button 114.

It is to be appreciated that the slider 116 may be freely moveable in a linear direction or may include a mechanism for incremental movements, e.g., a ratchet movement, to prevent an operator of the apparatus 100 from over extending the blade 118. By employing a mechanism for incremental movements of the blade 118, the operator will have greater control over the length of the exposed blade 118 to avoid damage to tissue at the surgical site.

An enlarged view of the distal end 106 of the outer tube 104 is also illustrated in FIG. 2B. Here, the blade 118 is coupled to the flow tube 122 which is held in place in the outer tube 104 by at least one seal 136. The at least one seal 136 prevents backflow of gas into tube 104 and housing 102. A cylindrical ceramic insert 138 is disposed in the distal end of the outer tube 104 to maintain the blade along the longitudinal axis of the apparatus 100 and provide structural support during mechanical cutting when the blade is exposed beyond the distal end of the outer tube 104.

The operational aspect of the apparatus 100 will now be described in relation to FIGS. 3A and 3B, where FIG. 3A shows an enlarged cross section of the apparatus and FIG. 3B illustrates a front view of the apparatus.

Referring to FIG. 3A, the flow tube 122 is disposed in the outer tube 104 with a cylindrical insulator 140 disposed around the flow tube 122. Slider 116 is coupled to the insulator 140 and is employed to extend and retract the blade 118. At the distal end 106 of the outer tube 104, the annular or ring shaped seal 136 and cylindrical ceramic insert 138 are disposed about the flow tube 122. As can be seen in FIG. 3B, the generally planar blade 118 is coupled to an inner circumference of the cylindrical flow tube 122 such that two gas passageways 142, 144 are formed on the both sides of the blade 118. As gas flows from the proximal end 103 of the housing through the flow tube 122, the gas will pass over the blade 118 out the distal end 106 of the outer tube 104.

When the blade is in the retracted position as shown in FIG. 3A, the apparatus 100 is suitable for generating plasma. In the retracted position, RF energy is conducted to a tip 146 of the blade 118 from an electrosurgical generator (not shown) via the flow tube 122. An inert gas, such as helium or argon, is then supplied to the flow tube from either the electrosurgical generator or an external gas source. As the inert gas flows over the sharp point 146 of the blade 118 held high voltage and high frequency, a cold plasma beam is generated.

Figure 4:
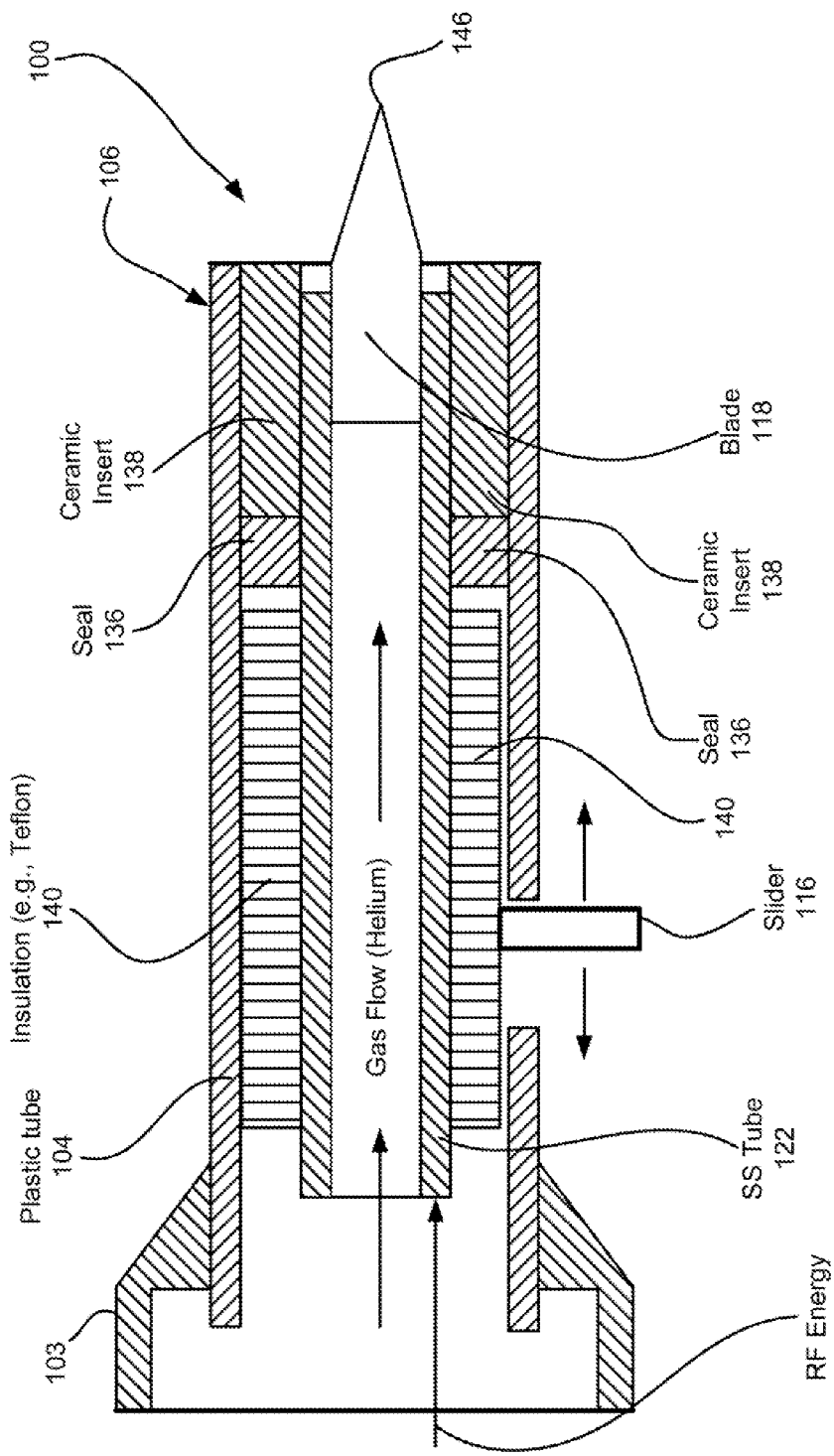
FIG. 4 is an enlarged cross sectional view of the electrosurgical apparatus shown in FIG. 3A with a blade extended.

Referring to FIG. 4, the blade 118 is advanced, via slider 116, so the tip 146 is extended past the distal end 106 of the outer tube 104. In this state, the blade 118 can be used for two cutting modes: mechanical cutting and electrosurgical cutting. In the mechanical cutting mode, RF or electrosurgical energy is not applied to the flow tube 122 or blade 118, and therefore, the blade 118 is in a de-energized state. In this mode, the blade 118 can be used excise tissue via mechanical cutting. After the tissue is removed, the blade 118 may be retracted via the slider 116 and electrosurgical energy and gas may be applied via button 114 to generate a cold plasma beam for cauterization, sterilization and/or hemostasis of the operative patient site.

In the electrosurgical cutting mode, the blade 118 is advanced and used while both electrically energized and with inert gas flow. This configuration resembles an electrosurgical knife approach, where the electrosurgical energy does the cutting. However, with the addition of the inert gas flow, cuts made show virtually no eschar, with very little collateral damage along the side walls of the cut. The cutting speed is considerably faster, with less mechanical cutting resistance as compared to when the knife blade is not electrically energized, i.e., the mechanical cutting mode. Hemostasis is also affected during this process.

Figure 5:
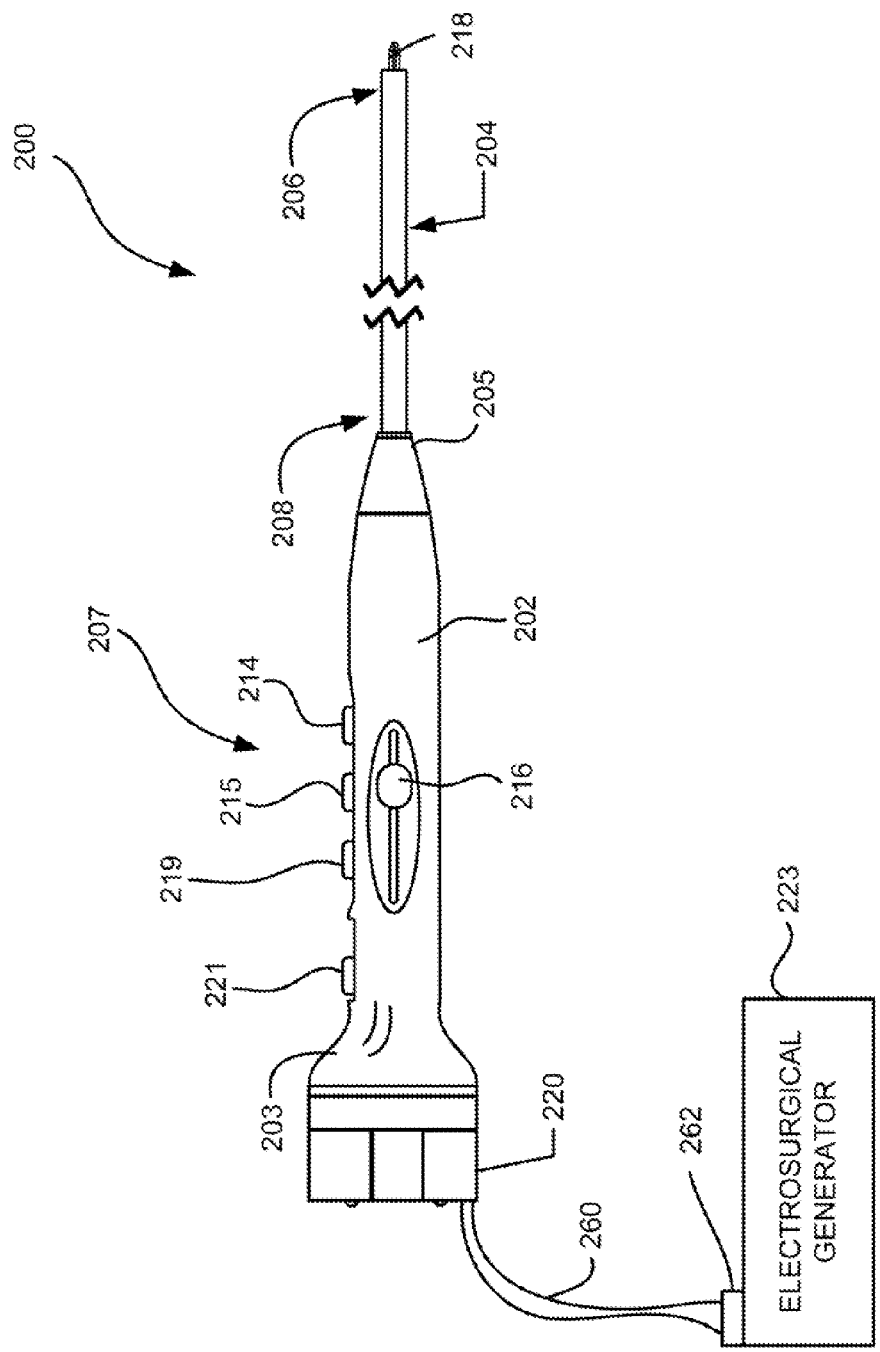
FIG. 5 is a side perspective view of an electrosurgical apparatus in accordance with another embodiment of the present disclosure.
Figure 6:
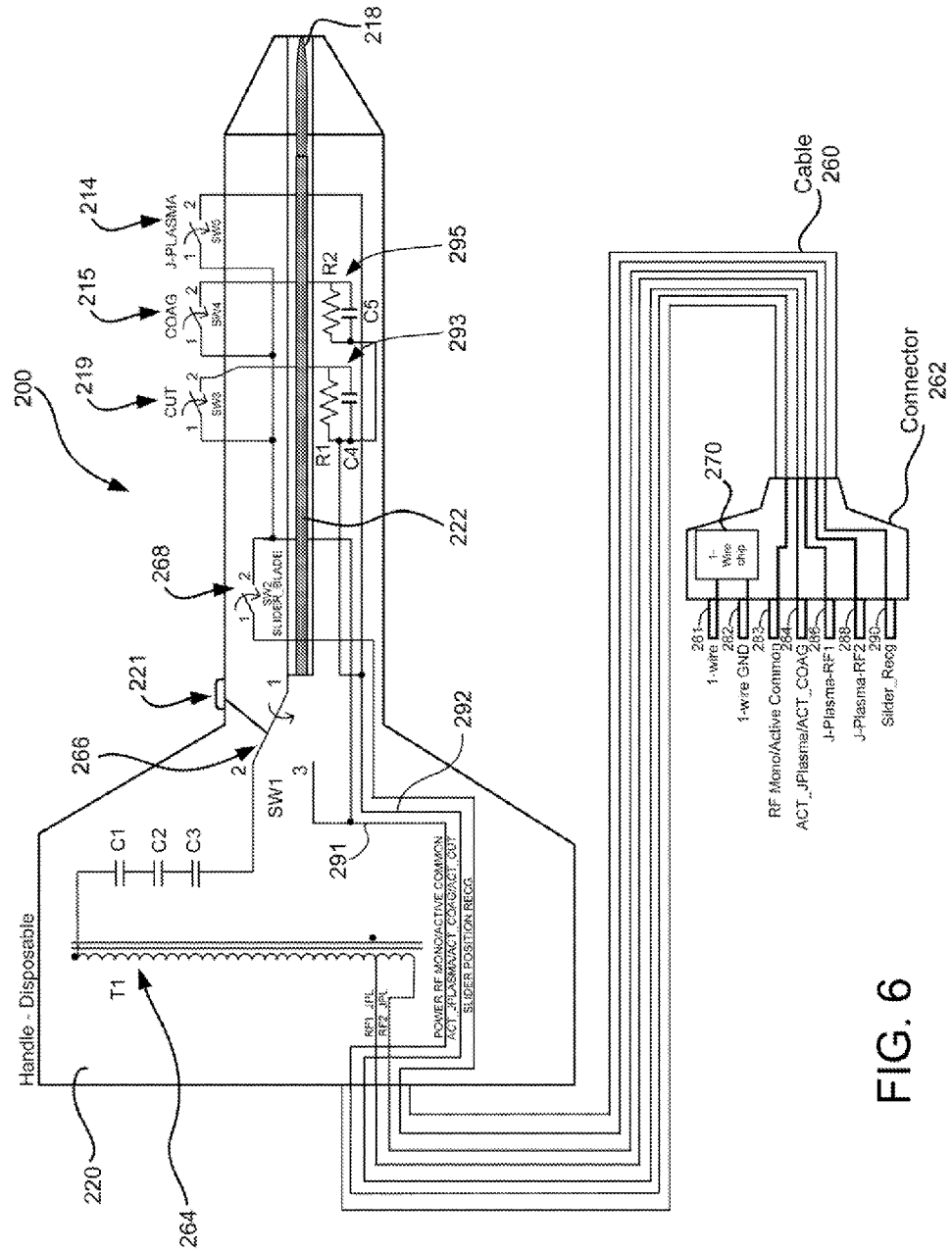
FIG. 6 is an electrical schematic diagram of the electrosurgical apparatus shown in FIG. 5.
Figure 7:
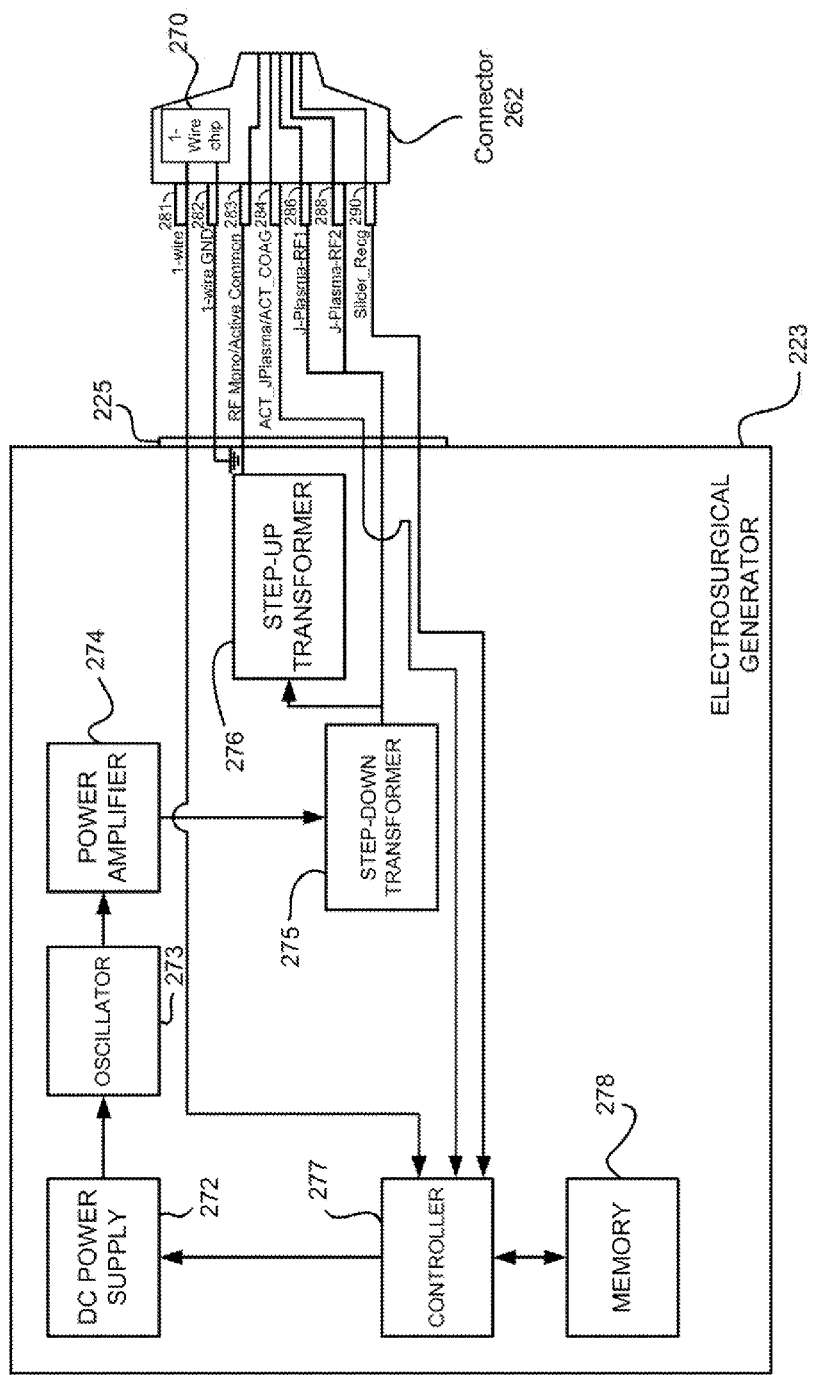
FIG. 7 is an electrical schematic diagram of an electrosurgical generator in accordance with an embodiment of the present disclosure.

Referring to FIGS. 5-7, an electrosurgical apparatus 200 in accordance with another embodiment of the present disclosure is illustrated. Generally, the apparatus 200 includes a housing 202 having a proximal end 203 and a distal end 205 and a tube 204 having an open distal end 206 and a proximal end 208 coupled to the distal end 205 of the housing 202, thereby forming a handpiece. The housing 202 includes a plurality of buttons 207, e.g., buttons 214, 215 and 219, and a first slider 216 and second slider 221. Activation of the first slider 216 will expose a blade 218 at the open distal end 206 of the tube 204, as described above. Activation of the second slider 221 sets the apparatus into different modes, as will be described below. Activation of the individual buttons 214, 215, 219 will apply electrosurgical energy to the blade 218 to affect different electrosurgical modes and, in certain embodiments, enable gas flow through an internal flow tube 222, as will be described in detail below. Additionally, a transformer assembly 220 is provided on the proximal end 203 of the housing 202 for coupling a source of radio frequency (RF) energy to the apparatus 200 via cable 260 and connector 262. The cable 260 includes a plurality of conductors for providing electrosurgical energy to the apparatus 200 and for communication signals to and from the apparatus 200 and an RF source, e.g., an electrosurgical generator 223. The connector 262 includes various pins, e.g., pins 281, 282, 283, 284, 286, 288 and 290, for coupling the connector 262 to corresponding port 225 on the generator 223, the details of which will be described below.

As can be seen in FIG. 7, the electrosurgical generator 223 includes a DC power supply 272, an oscillator 273, a power amplifier 274, a step-down transformer 275 and a step-up transformer 276 for supplying power to the apparatus 200. The electrosurgical generator 223 further includes a controller 277 and memory 278.

Referring back to FIG. 6, the transformer assembly 220 includes transformer T1 264, e.g., a step-up transformer, and at least one switch 266, which is controlled by the second slider 221. The switch 266 is coupled on one end to the conductive flow tube 222 and the other end of the switch 266 is adjustable between an output of transformer 264 and an output received directly from the generator 223 via pin 283, e.g., signal POWER_RF_MONO/ACTIVE_COMMON. The switch 266 is controlled by the second slider 221 located on the external surface of the housing 202. The second slider 221 may include a mechanism to lock the slider 221 in a particular position. In one embodiment, the second slider 221 controls the switch 266 and is interlocked to disable other buttons and/or sends signals to the generator 223 for selecting a mode. In another embodiment, the switch 266 may be coupled to the first slider 216 to select a mode based on the position of the conductive flow tube 222 and/or blade 218.

In a first position, switch 266 is coupled between terminal 2 and terminal 1 wherein an output of the transformer 264 is coupled to the conductive flow tube 222. In a second position, switch 266 is coupled between terminal 3 and terminal 1 wherein an output of the generator 223, i.e., an external source, is coupled to the conductive flow tube 222.

It is to be appreciated that switch 266 is to have very low stray capacitance between terminals 1 and 2 and terminals 1 and 3 to avoid mutual coupling of the transformer 264 and the lines from the generator. Step-up transformers 264 and 276 are both operated from the output of step-down transformer 275, so their outputs can be configured as to be in-phase. As a result, the potential difference between switch 266 contacts 2 and 3 can be small, depending on the load placed on either of those transformers. This will minimize potential arc-over between those contacts. Stray capacitance may, in general, be minimized by using a small contact area for contacts 2 and 3 of switch 266 (comparable to the area of the plates of a capacitor) within the limits of their current carrying requirements. Maximizing the distance between contacts 2 and 3 of switch 266 when it is in an open state will also reduce stray capacitance (comparable to the distance between two plates of a capacitor).

Furthermore, the position of the blade 218 determines the position of switch 268. Switch 268 is coupled to the connector 262 via a conductor, e.g., SLIDER_POSITION_RECG, which signals the generator as to the position of the blade 218 via pin 290. It is to be appreciated that switch 268 may be toggled between an open and closed position by being either directly or indirectly coupled to the slider 216 or the conductive flow tube 222.

Activation of the individual buttons 214, 215, 219 will apply electrosurgical energy to the blade 218 to affect different electrosurgical modes depending on the position of the blade 218. In the embodiment shown, button 214 is configured for activating the J-Plasma mode, button 215 is configured for activating a COAG (or coagulation) mode and button 219 is configured for activating a CUT mode. Two wires or conductors 291, 292 are used to recognize which of the buttons or switches 214, 215 or 219 are closed or activated. One of these wires, i.e., wire 291 coupled to pin 283, is also employed for applying RF power to blade 218 when switch 266 is coupled between terminal 3 and terminal 1 wherein an output of the generator 223 is coupled to the conductive flow tube 222. The other wire, i.e., wire 292 coupled to pin 284, is employed to allow controller 277 to sense which switch or button 214, 215 or 219 is activated. For example, when switch 214 is activated, the controller 277 senses approximately 0 ohms; when switch 215 is activated, the controller 277 senses the parallel combination of resistor R2 and capacitor C5 at a given frequency; and when switch 219 is activated, the controller 277 senses the parallel combination of resistor R1 and capacitor C4 at a given frequency When the slider 216 retracts the blade 218 inside the opening of the tube 204, the J-Plasma mode is selected. In this mode, the J-Plasma button 214 is enabled while the COAG button 215 and CUT button 219 are mechanically and/or electrically disabled. Although not shown, the COAG button 215 and CUT button 219 may be mechanically disabled by a switch, relay, etc. In the J-Plasma mode, switch 266 is coupled between terminal 2 and terminal 1 wherein an output of the transformer 264 is coupled to the conductive flow tube 222. Additionally, switch 268 is closes, which signals the controller 277 in the generator 223 as to the position of the blade 218 and that the handpiece is in J-Plasma mode. Upon activation of button 214, a signal is sent to the generator 223 via pin 284, e.g., ACT_JPLASMA/ACT_COAG/ACT_CUT, to initiate plasma generation. Subsequently, the generator supplies power via pin 286 along line RF1_JPL and via pin 288 along line RF2_JPL, via the step-down transformer 275 which provides power to step-up transformer 264. Furthermore, in J-Plasma mode, activation of button 214 initiates the flow of gas through the conductive flow tube 222. It is to be appreciated that in one embodiment the generator 223 coupled to the handpiece 200 may include an internal gas flow controller which receives the signal. In another embodiment, the gas flow controller is located externally of the generator 223 but may receive the gas activation signal from the generator. In a further embodiment, the gas flow controller is located externally of the generator 223 but may receive the gas activation signal from the handpiece itself via hardwired or wireless means.

When the slider 216 extends the blade 218 beyond the opening of the tube 204, the COAG/CUT mode is selected, also known as the general electrosurgery mode. In this mode, the COAG button 215 and CUT button 219 are enabled while the J-Plasma button 214 is mechanically and/or electrically disabled. Although not shown, the J-Plasma button 214 may be mechanically disabled by a switch, relay, etc. In the COAG/CUT mode, switch 266 is coupled between terminal 3 and terminal 1 wherein an output of the step-up transformer 276 in the generator 223 is coupled to the conductive flow tube 222, i.e., the transformer 264 is bypassed. Upon activation of buttons 215 or 219, a signal is sent to the generator via line ACT_JPLASMA/ACT_COAG/ACT_CUT to initiate supply of electrosurgical energy. Subsequently, the generator supplies power via pin 283 along line POWER_RF MONO/ACTIVE COMMON, which provides power to the conductive flow tube 222.

It is to be appreciated that the two step-up transformers 264, 276 (i.e., transformer 264 in the handpiece 200 for the J-Plasma mode and transformer 276 in the generator 223 for the general electrosurgery mode) have two different power curves. That is their output impedances are matched for different loading conditions. The J-Plasma transformer 264 in the handpiece 200 will put out higher voltages than the electrosurgery transformer 276 in the generator 223, but the J-Plasma transformer 264 is also matched for a higher output impedance for the combined tissue load and the plasma beam impedances in series. The electrosurgery transformer 276 back in the generator 223 has a lower output voltage, but higher current capability and its output impedance is matched to the lower impedance value of an electrosurgical blade 218 in direct contact with tissue. Exemplary values for the output in J-Plasma mode are 10 kilo ohm output impedance, 4 kV to 6 kV peak-to-peak and 140 mA, where the exemplary values for the output in electrosurgery mode are 150-250 ohm output impedance, 300 V to 6.5 kV peak-to-peak and 1.5 Amps. It is to be appreciated these exemplary values are for illustrative purposes only and in use the values may vary.

In some embodiments, gas may be provided to the handpiece 200 when in COAG/CUT mode. In one embodiment with the blade 218 extended, a mode button may be provided on the generator to enable gas to flow, e.g., CUT with gas. In another embodiment, when the blade 218 is retracted, fulguration or fulguration with gas may be enabled from a button in the generator.

In one embodiment, the connector 262 includes a one-wire chip 270, e.g., a memory, including information associated with the handpiece or applicator so the generator may recognize the handpiece. When coupled to a generator via pins 281 and 282, the controller 277 of generator 223 reads the information contained on the chip 270 and may perform or execute instructions based on the handpiece type. In other embodiment, the chip 270 may have read/write capabilities where the chip 270 can store how many times the handpiece has been used and provide that information to the generator. In certain embodiments, the controller 277 of generator 223 may store or write the number of uses of the apparatus 200 in memory 278 and determine that the handpiece 200 may no longer be used based on a predetermined use limit. In a further embodiment, the chip 270 may store application specific information for the handpiece that is to be loaded into the generator, e.g., a specific power profile of the handpiece. In another embodiment, the chip 270 may store information relating to the gas type to be used with the handpiece, e.g., Argon, Helium, etc. In this embodiment, the generator may provide an indication (or prevent operation) if the gas supplied does not match the type designated for the handpiece.

Figure 8:
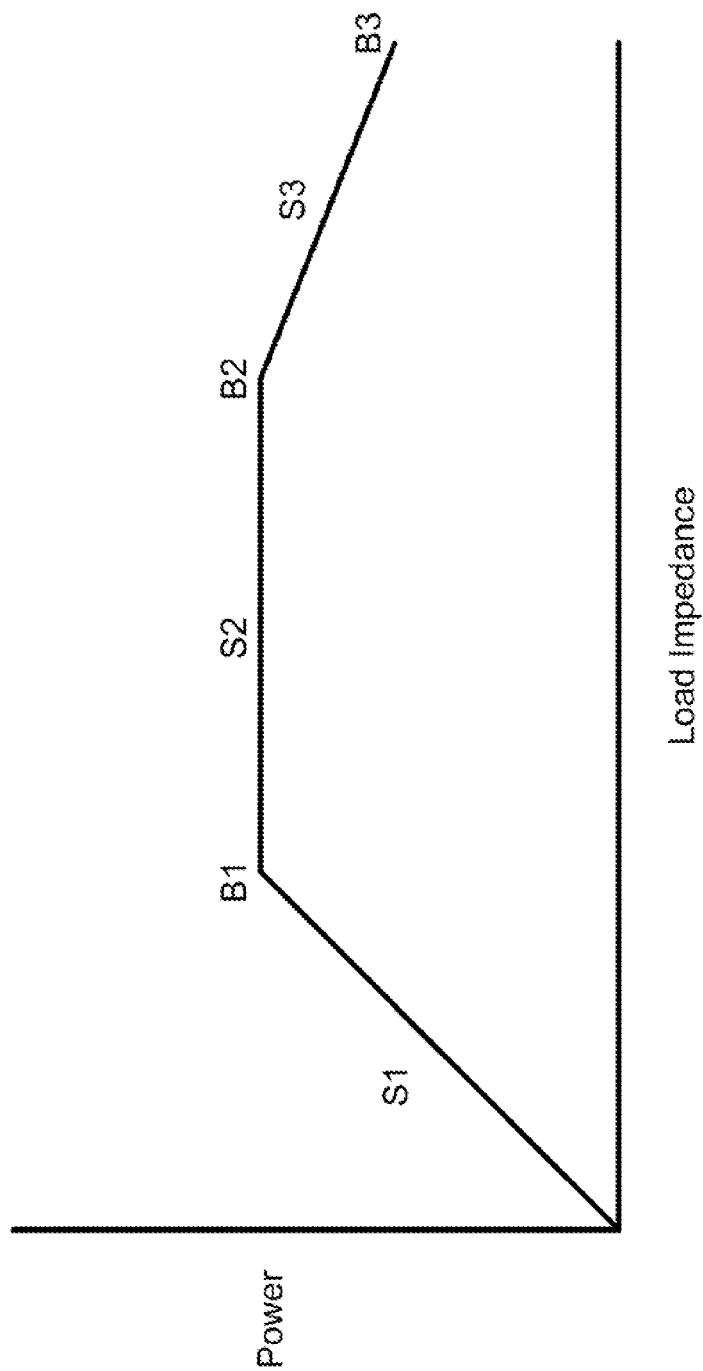
FIG. 8 illustrates a generalized generator unit's output power curve.

In one embodiment, the chip 270 may store application specific information for the handpiece that is to be loaded into the generator, e.g., a specific power profile of the handpiece. While maximum and/or minimum power preset values establish overall operational boundaries for a given applicator, greater applicator safety and effectiveness can be realized by a pre-defined power curve specific to an applicator class or even a particular individual applicator. Typically, a power curve shows the relationship between the generator unit's output power and the load impedance. A generalized power curve is illustrated in FIG. 8.

The power curve can be approximated by three segments. The first is the constant current segment, shown as S1 in FIG. 8. The internal output impedance of the generator unit limits the output power under this heavily loaded condition. Next is the constant power segment, S2 FIG. 8, where the load impedance more closely matches the generator unit's internal output impedance. Last is the constant voltage segment, S3 in FIG. 8, where the load impedance is significantly higher than the generator unit's output impedance.

Electrosurgical applicator working electrodes may have different surface areas, or plasma-beam applicators may have different beam diameters, configurations, or beam lengths which require associated power curves for enhanced safety and effectiveness. The automatic applicator identifier can contain a power curve specific to that applicator class or even tailored to a given particular applicator. This applicator-specific power curve information is downloaded to the generator unit 223, which then modifies its operational output power curve to match the requirements of a given applicator. Note that the generator unit's intrinsic output power curve represents a maximum overall set of values, from which the downloaded requested power curve can be a reduced value subset.

The stored power curve in the automatic applicator identifier can consist of a potentially large array of data points from which the required power curve can be reconstructed by the generator unit. A more compact representation, as illustrated in FIG. 8, need only contain the three breakpoints B1, B2, and B3 of the associated three segments S1, S2, and S3 respectively.

In an alternative embodiment, another stored power curve may describe a relationship between a displayed value of a selected power setting to an internal pulse width within the generator unit, which, in turn, produces a specific power output. It is to be appreciated that this power curve would include that same general features as the above described power curve, i.e., this power curve will have segments and breakpoints similar to those illustrated in FIG. 8. This power curve may also be stored as a look-up table.

Figure 9:
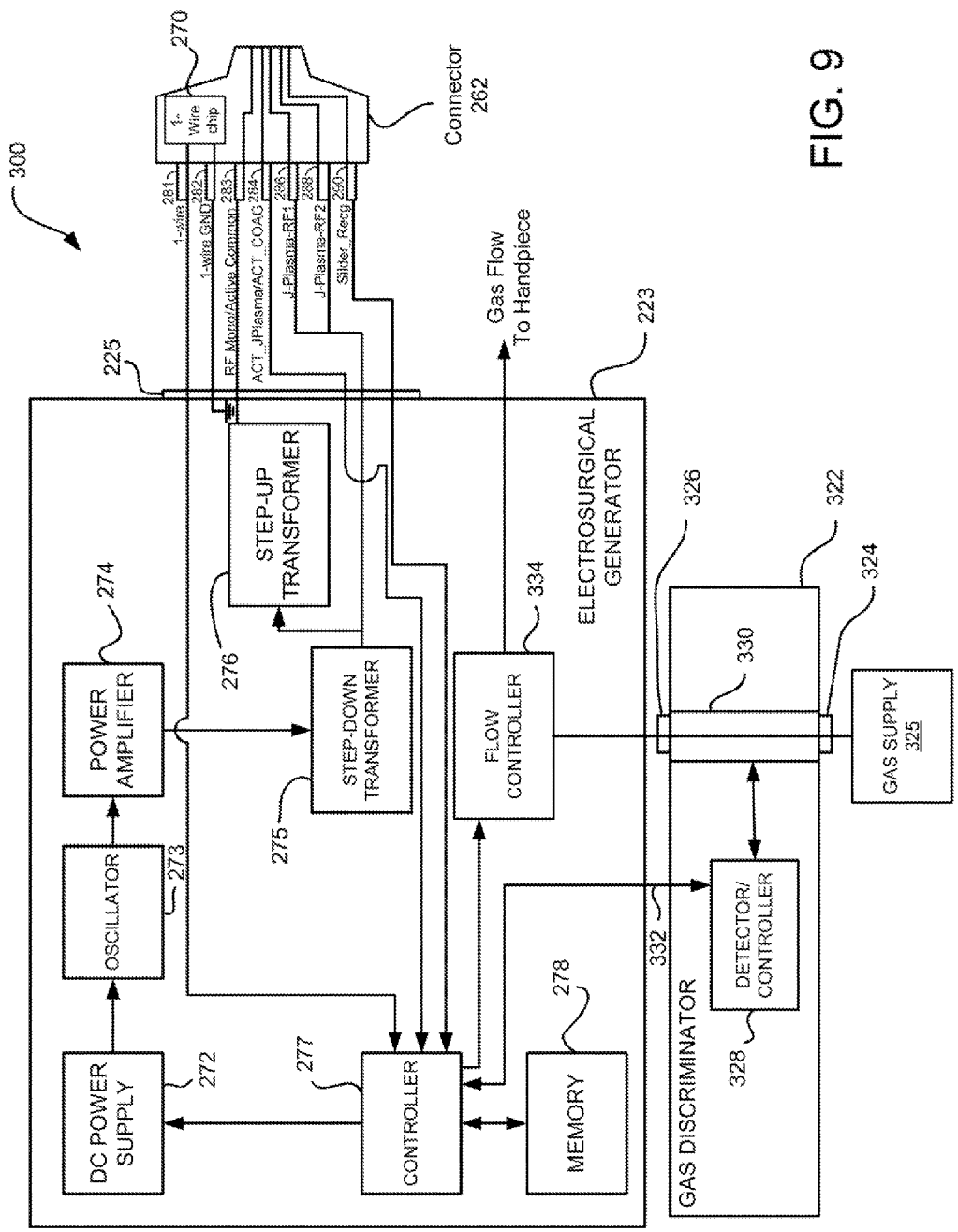
FIG. 9 is an electrical schematic diagram of an electrosurgical generator in accordance with another embodiment of the present disclosure.

In another embodiment, the chip 270 may store information relating to the gas type to be used with the handpiece, e.g., Argon, Helium, etc. In one embodiment, the generator or ancillary device determines if the gas supplied matches the gas type designated for the handpiece as indicated by the chip 270. Systems and methods for determining a gas type are disclosed in commonly owned U.S. Patent Publication No. 2014/0005665, the contents of which are hereby incorporated by reference. Referring to FIG. 9, an electrosurgical system 300 is illustrated including an electrosurgical generator (ESU) 223, a gas discriminator 322 and a connector of an electrosurgical handpiece 262, e.g., a plasma generator. The gas discriminator 322 shown in FIG. 9 may determine a gas type by any of the methods described in U.S. Patent Publication No. 2014/0005665. As shown in FIG. 9, the gas discriminator 322 generally includes a gas input 324 coupled to a gas supply 325, a gas output 326 and a detector/ controller 328 coupled to a tube or chamber 330 for detected a type of gas flowing therethrough. The detector/controller 328 provides an output control signal 332, for example, indicative of the gas type, a GO signal, No Go signal, etc. The output control signal 332 is transmitted to the controller 277 of the electrosurgical generator 223. The electrosurgical generator 223 further includes a flow controller 334 for controlling the flow of gas to an electrosurgical handpiece. The flow controller 334 is coupled to the controller 277 and receives control signals from the controller 277 based on an algorithm or software function stored in memory 278. In one embodiment, the flow controller 334 may receive a control signal from the controller 277 based on a second control signal, e.g., signal 332, received at the controller 277 from the gas discriminator 322. For example, upon coupling an electrosurgical handpiece via connector 262 to generator 223, the controller 277 reads from the chip 270 the type of gas to be used with a specific handpiece. The controller 277 then transmits the gas type to the gas discriminator 322. If the gas discriminator 322 determines that an expected gas is fed into the gas discriminator 322 and/or handpiece, the gas discriminator 322 transmits a "Go" signal to the controller 277 which subsequently enables the flow controller 334 and enables the RF output stage. Alternatively, if the gas discriminator 322 determines that the gas fed into the gas discriminator 322 and/or handpiece is a gas other than the expected gas, the gas discriminator 322 transmits a "No Go" signal to the controller 277 which subsequently disables the flow controller 334 and disables the RF output stage. It is to be appreciated that the control signal 332 may simply cause the electrosurgical generator to shutdown the RF output stage in certain embodiments where a flow controller 334 is not provided. It is to be further appreciated that the control signal 332 generated by the gas discriminator 322 may be coupled to the handpiece to disable the handpiece when necessary.

In another embodiment, the gas discriminator 322 determines the type of gas, e.g., Helium, Argon, etc., and transmits the determined gas type to controller 277. The controller 277 then determines if the determined gas type matches the specific gas type for the handpiece as read from the chip 270. If the gas types match, the controller 277 enables operation of the generator and handpiece; otherwise, the controller 277 disables the generator and/or handpiece. Other methods to disable or stop an electrosurgical procedure, device or apparatus via the output of the gas discriminator are contemplated to be within the scope of the present disclosure. It is to be appreciated that, in some embodiments, gas discriminator 322 may be coupled externally to electrosurgical generator 223 (for example, as shown in FIG. 9). Alternatively, it is to be appreciated that, in other embodiments, gas discriminator 322 may be disposed within electrosurgical generator 223.

Certain types of medical device applicators, plasma-beam applicators in particular, may have tuned resonant elements within the applicator. It is often a difficult and time consuming task to fine tune the resonant elements in the applicator to match the output frequency of the generator unit for optimum performance, safety, and effectiveness. Small manufacturing variations in the applicator can have significant impact in performance, especially where the resonant Q factor is high. Rather than attempt to fine tune the applicator, the actual resonant frequency of the applicator (or components therein) is measured, and the measured value is stored in the automatic applicator identifier chip 270 in accordance with the present disclosure. The measured resonant frequency value of the applicator is downloaded to the generator unit and is then used to fine tune at least one frequency component of the generator unit to optimize the performance of that particular applicator.

For example, in one embodiment, of particular importance is the resonant frequency of the high voltage output transformer, e.g., step-up transformers 264. Due to the high resonant Q of this transformer, a slight mismatch of generator operating frequency and resonant frequency of a given transformer will produce significant reduction in the output voltage, affecting overall performance. The effect of manufacturing tolerances from one transformer to another, which would otherwise be insignificant, are magnified by the high Q factor of these transformers. Rather than meticulously attempt to trim the resonant frequency of each transformer individually, to match the operating frequency of the generator, the actual resonant frequency of each transformer is determined, and this value is stored in the identifier chip 270. This value is then read by the controller 277 of generator 223, which adjusts its operating frequency to match that of a particular transformer. In one embodiment, the generator's operating frequency is adjusted via oscillator 273 although other methods to adjust the frequency are contemplated to be within the scope of the present disclosure.

In another embodiment, applicator 200 includes at least one reactive switching element 293, 295 to employ a multi-button activation scheme. An exemplary multi-button activation scheme is shown and described in commonly-owned U.S. Patent Publication No. 2014/0018795, the contents of which are hereby incorporated by reference. U.S. Patent Publication No. 2014/0018795 describes a multi-button activation scheme where at least three input buttons are disposed on a housing of an applicator while minimizing the number of wires or conductors between the applicator and generator. As shown in FIG. 6, input buttons 214, 215, 219 are coupled to reactive switching elements 293, 295 which are further coupled to activation sense circuits (not shown) disposed in the generator. The activation sense circuits are configured to distinguish which input button has been activated. The activation sense circuits include an oscillator, where a frequency of the oscillator is tuned to be in resonance with the reactive switching elements of the applicator. In certain embodiments of the present disclosure, the resonant frequency value of the reactive switching elements of a particular applicator are determined and store in the chip 270. Upon coupling the applicator to an appropriate generator, a controller 277 of the generator reads the resonant frequency values for the particular applicator and tunes the frequency of the activation sense circuit in the generator. By enabling the generator to self-tune for a particular applicator, calibration and setup time for a procedure is reduced.

In certain embodiments, the automatic applicator identifier chip or memory 270 has read/write capabilities. Having read/write capabilities enables an electrosurgical generator to write data or values to the chip 270. For example, upon coupling the applicator to the electrosurgical generator, an initial start time of the applicator may be written to the chip 270 by the electrosurgical generator. In one embodiment, a timestamp is sent to the chip, and stored therein, during an initial handshake between the applicator and generator. The timestamp may then be read from the chip 270 by the electrosurgical generator to determine accumulated run time, activation duration, elapsed time from first use, etc. The determined accumulated run time may then be compared by the controller 277 to a maximum accumulated runtime, which is also stored on the chip 270, to determine if this maximum has been reached for the applicator. Similarly, a maximum activation duration may be read from the chip 270 and compared to the activation duration as determined by the electrosurgical generator. The electrosurgical generator may disable the applicator when certain predetermined limits or maximums are reached.

In another embodiment, a portion of the chip 270 may be designated as a counter where the electrosurgical generator updates the counter upon, for example, each use of the applicator, each use of the applicator for a specific procedure, each activation of the applicator, etc. The electrosurgical generator may reads a specific counter along with an associated predetermined maximum to determine if the maximum value has been exceeded to disable the applicator. For example, upon each activation of the applicator, the electrosurgical generator updates an associated activation counter in chip 270. Prior to a subsequent activation, the electrosurgical generator reads a predetermined maximum number of activations stored on the chip 270 and compares the activation counter to the predetermined maximum. If the activation counter exceeds the predetermined maximum number of activations, the electrosurgical generator may disable the applicator or not provide power thereto.

In a further embodiment, the automatic applicator identifier chip or memory wirelessly communicates to the generator. The wireless connection will operate under any of the various wireless protocols including but not limited to Bluetooth™ interconnectivity, infrared connectivity, radio transmission connectivity including computer digital signal broadcasting and reception commonly referred to as Wi-Fi or 802.11.X (where x denotes the type of transmission), or any other type of communication protocols, communication architecture or systems currently existing or to be developed for wirelessly transmitting data including spread spectrum 900 MHz, or other frequencies, Zigbee, or any mesh enabled wireless communication.

Figure 10:
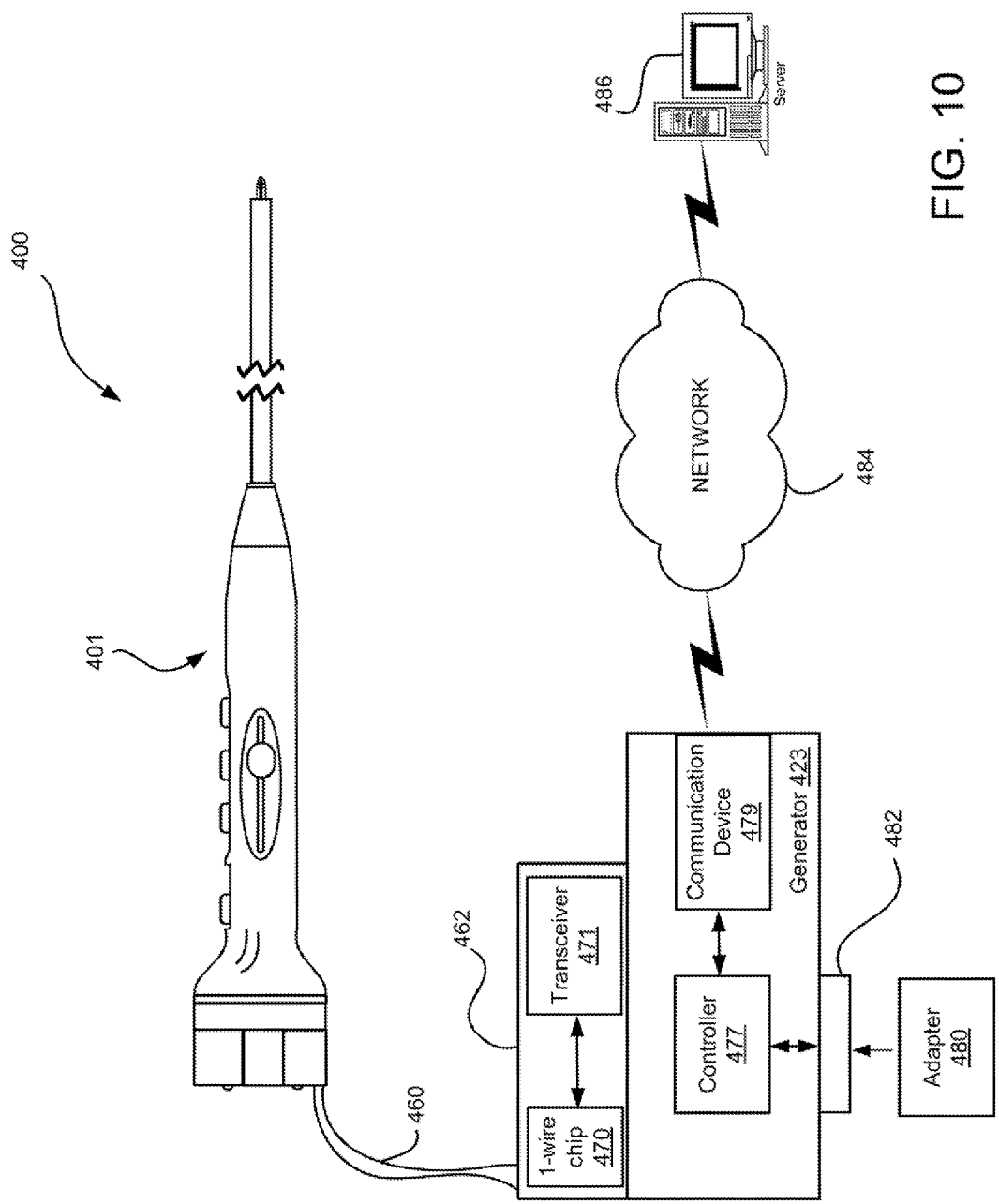
FIG. 10 illustrates an electrosurgical system in accordance with a further embodiment of the present disclosure.

Referring to FIG. 10, an electrosurgical apparatus 400 in accordance with another embodiment of the present disclosure is illustrated. In this embodiment, the applicator or handpiece 401 is coupled to electrosurgical generator 423 via cable 460 and connector 462. The connector 462 includes a chip or memory 470, as described above, coupled to a wireless transceiver 471. The generator 423 further includes a communication device 479 configured to wirelessly communicate with the transceiver 471. In use, the communication device 479 receives data from the transceiver 471 and sends the received data to the controller 477 to achieve at least the various control modes described above.

It is to be appreciated that older model generators may not include a wireless communication device. For such older models, an external wireless adapter 480 may be coupled to the generator 423 via an appropriate communication port 482, e.g., a USB port, FireWire port, etc. The external wireless adapter 480 communicates wirelessly to transceiver 471 and sends the data received from the transceiver 471 to controller 477.

In a further embodiment, the communication device 479 of generator 423 enables communications to a server or other computing device for reporting details of the use of a particular applicator to ensure traceability of the applicator. The communication device 479 may be a modem, network interface card (NIC), wireless transceiver, etc. The communication device 479 will perform its functionality by hardwired and/or wireless connectivity. The hardwire connection may include but is not limited to hard wire cabling e.g., parallel or serial cables, RS232, RS485, USB cable, Firewire (1394 connectivity) cables, Ethernet, and the appropriate communication port configuration. The wireless connection will operate under any of the various wireless protocols including but not limited to Bluetooth™ interconnectivity, infrared connectivity, radio transmission connectivity including computer digital signal broadcasting and reception commonly referred to as Wi-Fi or 802.11.X (where x denotes the type of transmission), satellite transmission or any other type of communication protocols, communication architecture or systems currently existing or to be developed.

The generator 423 may be connected to a communications network 484, e.g., the Internet, by any means, for example, a hardwired or wireless connection, such as dial-up, hardwired, cable, DSL, satellite, cellular, PCS, wireless transmission (e.g., 802.11a/b/g), etc. It is to be appreciated that the network may be a local area network (LAN), wide area network (WAN), the Internet or any network that couples a plurality of computers to enable various modes of communication via network messages. Furthermore, the server will communicate using various protocols such as Transmission Control Protocol/Internet Protocol (TCP/IP), File Transfer Protocol (FTP), Hypertext Transfer Protocol (HTTP), etc. and secure protocols such as Hypertext Transfer Protocol Secure (HTTPS), Internet Protocol Security Protocol (IP-Sec), Point-to-Point Tunneling Protocol (PPTP), Secure Sockets Layer (SSL) Protocol, etc.

In certain embodiments, the generator 423 reads the unique identification identifier from chip 470 and transmits the identifier via the communication device 479 over the network 484 to a server or computing device 486. Server 486 may be maintained by a facility such as a hospital for inventory control. The server 486 may enter into a database and keep track of the number of uses of the applicator. In certain embodiments, the server 486 may determine if the applicator has reached a predetermined number of uses, and if so, the server 486 sends a control signal or command to the generator 423 to prevent use of the applicator and provide an local indication on a display of the generator.

It is to be appreciated that connector 262/462 is not limited to use with the electrosurgical applicator described above. Connector 262/242 may be configured to be used with many types of electrosurgical applicators, such as electrosurgical pencils, vessel sealers, etc. For example, an exemplary electrosurgical applicator is shown and described in commonly-owned U.S. Patent Publication No. 2014/0018795, the contents of which are hereby incorporated by reference.

It is to be appreciated that the various features shown and described are interchangeable, that is, a feature shown in one embodiment may be incorporated into another embodiment.

While the disclosure has been shown and described with reference to certain preferred embodiments thereof, it will be understood by those skilled in the art that various changes in form and detail may be made therein without departing from the spirit and scope of the disclosure as defined by the appended claims.

Furthermore, although the foregoing text sets forth a detailed description of numerous embodiments, it should be understood that the legal scope of the invention is defined by the words of the claims set forth at the end of this patent. The detailed description is to be construed as exemplary only and does not describe every possible embodiment, as describing every possible embodiment would be impractical, if not impossible. One could implement numerous alternate embodiments, using either current technology or technology developed after the filing date of this patent, which would still fall within the scope of the claims.

It should also be understood that, unless a term is expressly defined in this patent using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. §112, sixth paragraph.

What is claimed is:

1. An electrosurgical apparatus comprising:
a housing having a passage extending therethrough, the housing having a proximal end and a distal end;
an electrically conducting tube having a proximal end and a distal end, the electrically conducting tube being disposed in the passage of the housing;
an insulating outer tube having a proximal end and a distal end, the outer tube disposed around the electrically conducting tube with the proximal end of the outer tube coupled to the distal end of the housing, the electrically conducting tube being movable along a longitudinal axis of the housing and outer tube;
an electrode coupled to the distal end of the electrically conducting tube, wherein at least the housing, electrically conducting tube, the insulating outer tube, and the electrode comprise an applicator, and
a connector configured for coupling the applicator to an electrosurgical generator, the connector including a memory configured to store parameters associated with the applicator, wherein at least a first parameter of the stored parameters is a type of gas associated with the applicator and the connector is configured to communicate the type of gas associated with the applicator to the electrosurgical generator, wherein the connector is further configured to receive a gas from the electrosurgical generator and provide the received gas to the electrically conducting tube when the type of gas associated with the applicator matches the gas provided by the electrosurgical generator.

2. The apparatus of claim 1, wherein the connector is configured to communicate at least one of the stored parameters to the electrosurgical generator via direct electrical path.

3. The apparatus of claim 1, wherein the connector includes a transceiver configured to wirelessly communicate at least one of the stored parameters to the electrosurgical generator.

4. The apparatus of claim 1, wherein communication between the connector and the electrosurgical generator is encrypted to prevent unauthorized modification of any of the stored parameters.

5. The apparatus of claim 1, wherein at least a second parameter of the stored parameters is a maximum and minimum power to be supplied to the applicator.

6. The apparatus of claim 1, wherein at least a second parameter of the stored parameters is a pre-defined power curve of the applicator.

7. The apparatus of claim 1, wherein the memory has read/write capabilities.

8. The apparatus of claim 7, wherein at least a second parameter of the stored parameters is a number of times the applicator has been used.

9. The apparatus of claim 1, wherein at least a second parameter of the stored parameters is a maximum and minimum gas flow rates associated with the applicator.

10. The apparatus of claim 1, wherein at least a second parameter of the stored parameters is a resonant frequency of at least one component of the applicator.

11. An electrosurgical apparatus comprising:
an electrosurgical generator coupled to an electrical power supply and configured to generate electrosurgical energy, the electrosurgical generator including a flow controller that supplies a gas to an applicator;
the applicator including:
a housing having a passage extending therethrough, the housing having a proximal end and a distal end;
an electrically conducting tube having a proximal end and a distal end, the electrically conducting tube being disposed in the passage of the housing;
an insulating outer tube having a proximal end and a distal end, the outer tube disposed around the electrically conducting tube with the proximal end of the outer tube coupled to the distal end of the housing, the electrically conducting tube being movable along a longitudinal axis of the housing and outer tube;
an electrode coupled to the distal end of the electrically conducting tube; and
a connector configured for coupling the applicator to the electrosurgical generator, the connector including a memory configured to store parameters associated with the applicator, wherein at least a first parameter of the stored parameters is a type of gas associated with the applicator and the connector is configured to communicate the type of gas associated with the applicator to the electrosurgical generator, wherein if the type of gas associated with the applicator matches a gas to be supplied by the flow controller, the flow controller supplies the gas to the applicator.

12. The apparatus of claim 11, wherein the electrosurgical generator reads at least one stored parameter from the memory of the connector.

13. The apparatus of claim 11, wherein the connector includes a transceiver configured to wirelessly communicate at least one of the stored parameters to the electrosurgical generator.

14. The apparatus of claim 13, further comprising an external adapter coupled to the electrosurgical generator, the external adapter configured to communicate with the transceiver in the connector.

15. The apparatus of claim 11, wherein communication between the connector and the electrosurgical generator is encrypted to prevent unauthorized modification of any of the stored parameters.

16. The apparatus of claim 11, wherein the electrosurgical generator is configured to communicate wirelessly with a remote server.

17. The apparatus of claim 11, wherein at least a second parameter of the stored parameters is a maximum and minimum power to be supplied to the applicator.

18. The apparatus of claim 17, wherein the electrosurgical generator is configured to modify the power being provided to the applicator based on communication from the memory indicating the maximum and minimum power that may be supplied to the applicator.

19. The apparatus of claim 11, wherein at least a second parameter of the stored parameters is a pre-defined power curve of the applicator.

20. The apparatus of claim 19, wherein the electrosurgical generator is configured to adjust the electrosurgical generator's operational output power curve to match the pre-defined power curve associated with the applicator based on communication from the memory indicating the pre-defined power curve of the applicator.

21. The apparatus of claim 11, further comprising a gas discriminator coupled to the electrosurgical generator, the gas discriminator configured to determine the type of gas being supplied by the flow controller, the gas discriminator is further configured to compare the determined type of gas being supplied by the flow controller with the type of gas associated with the applicator.

22. The apparatus of claim 21, wherein the gas discriminator is configured to prevent further operation of at least one of the applicator and electrosurgical generator if the gas discriminator determines the type of gas associated with the applicator is different than the type of gas being supplied by the flow controller.

23. The apparatus of claim 21, wherein the electrosurgical generator is configured to discontinue operation of the electrosurgical generator if the electrosurgical generator receives communication from the gas discriminator that the type of gas associated with the applicator is different than the type of gas being supplied by the flow controller.

24. The apparatus of claim 11, wherein at least a second parameter of the stored parameters is a resonant frequency of at least one component of the applicator.

25. The apparatus of claim 24, wherein the electrosurgical generator is configured to adjust at least one frequency of the electrosurgical generator to match the resonant frequency of the at least one component of the applicator based on communication from the memory indicating the resonant frequency of the at least one component of the applicator.

26. The apparatus of claim 11, wherein the electrosurgical generator writes time parameters associated to the applicator to the memory.

27. The apparatus of claim 11, wherein the electrosurgical generator updates a counter in the memory upon each use of the applicator.

28. The apparatus of claim 11, wherein the memory is a one-wire serial memory that is configured to communicate with the electrosurgical generator using a one-wire serial communication protocol.

29. An electrosurgical apparatus comprising:
an electrosurgical generator coupled to an electrical power supply and configured to generate electrosurgical energy; and
an applicator that supplies the electrosurgical energy to a surgical site including at least a connector configured for coupling the applicator to the electrosurgical generator, the connector including a memory configured to store parameters associated with the applicator, wherein at least a first parameter of the stored parameters is a type of gas associated with the applicator; and
a gas discriminator coupled to the electrosurgical generator, the gas discriminator configured to determine the type of gas being supplied to the applicator, compare the determined type of gas being supplied to the applicator with the type of gas associated with the applicator, and prevent further operation of at least one of the applicator and electrosurgical generator if the discriminator determines the type of gas associated with the applicator is different than the type of gas being supplied to the applicator.

* * * * *